(12) United States Patent
Oron et al.

(10) Patent No.: US 9,649,505 B2
(45) Date of Patent: May 16, 2017

(54) LOW-LEVEL ENERGY LASER THERAPY

(71) Applicant: Ramot at Tel Aviv University Ltd., Tel Aviv, IL (US)

(72) Inventors: Uri Oron, Rishon Lezion (IL); Hana Tuby, Bney Brak (IL)

(73) Assignee: RAMOT AT TEL AVIV UNIVERSITY LTD., Tel Aviv (IL)

( * ) Notice: Subject to any disclaimer, the term of this patent is extended or adjusted under 35 U.S.C. 154(b) by 0 days.

(21) Appl. No.: 15/130,979

(22) Filed: Apr. 17, 2016

(65) Prior Publication Data

US 2016/0228725 A1  Aug. 11, 2016

Related U.S. Application Data

(62) Division of application No. 13/264,755, filed as application No. PCT/IB2010/052133 on May 13, 2010, now Pat. No. 9,345,902.

(60) Provisional application No. 61/179,376, filed on May 19, 2009.

(51) Int. Cl.
*A61N 5/06* (2006.01)
*A61N 5/067* (2006.01)

(52) U.S. Cl.
CPC ......... *A61N 5/0613* (2013.01); *A61N 5/0601* (2013.01); *A61N 5/0618* (2013.01); *A61N 2005/067* (2013.01); *A61N 2005/0612* (2013.01); *A61N 2005/0643* (2013.01); *A61N 2005/0651* (2013.01); *A61N 2005/0659* (2013.01); *A61N 2005/0662* (2013.01)

(58) Field of Classification Search
None
See application file for complete search history.

(56) References Cited

U.S. PATENT DOCUMENTS

| | | | |
|---|---|---|---|
| 5,733,541 A * | 3/1998 | Taichman | C07K 14/52 424/93.1 |
| 2003/0125782 A1 * | 7/2003 | Streeter | A61N 5/0616 607/88 |
| 2009/0124958 A1 | 5/2009 | Li et al. | |

OTHER PUBLICATIONS

U.S. Appl. No. 15/214,525 Office Action dated Sep. 23, 2016.

* cited by examiner

*Primary Examiner* — Brian T Gedeon
*Assistant Examiner* — Ankit D Tejani
(74) *Attorney, Agent, or Firm* — D.Kligler IP Services Ltd.

(57) ABSTRACT

Methods and systems (10, 54, 72) are provided for administering phototherapy to an injured tissue in a living subject by delivering visible or infrared biostimulatory energy to bone marrow at a dose sufficient to cause mesenchymal stem cells to appear in the injured tissue. The energy may be coherent light and can be administered transcutaneously, subcutaneously, or via an intramedullary probe (74). The technique is useful for treating many types of tissue injury, including ischemic cardiac and renal conditions.

25 Claims, 4 Drawing Sheets

LOW-LEVEL ENERGY LASER THERAPY

CROSS-REFERENCE TO RELATED APPLICATIONS

This application is a division of U.S. patent application Ser. No. 13/264,755 filed Oct. 17, 2011, in the national phase of PCT Patent Application PCT/IB2010/052133, filed May 13, 2010, which claims the benefit of U.S. Provisional Patent Application No. 61/179,376, filed May 19, 2009, which is incorporated herein by reference.

BACKGROUND OF THE INVENTION

1. Field of the Invention

This invention relates to the controlled application of therapeutic light energy. More particularly, this invention relates to the therapeutic irradiation of marrow-containing bone using infrared light and energy of other wavelengths.

2. Description of the Related Art

The meanings of certain acronyms and abbreviations used herein are given in Table 1.

TABLE 1

Acronyms and Abbreviations

| | |
|---|---|
| ATP | adenosine tri-phosphate |
| BM | bone marrow |
| ECHO | echocardiographic |
| ICR | imprinting control region |
| IR | infrared |
| IRI | Ischemia reperfusion injury |
| LAD | anterior descending branch of left coronary artery |
| LED | light-emitting diode |
| LLLT | low level laser therapy |
| LV | Left ventricle |
| MI | myocardial infarction |
| MSC | mesenchymal stem cell |
| SEM | standard error of the mean |

The bone marrow is a complex tissue featuring several different types of primitive cells: hematopoietic stem cells, mesenchymal stem cells (MSCs), endothelial progenitor cells, side population cells, and multipotent adult progenitor cells. Like other stem cells, mesenchymal stem cells are capable of multilineage differentiation from a single cell and in vivo functional reconstitution of injured tissues. One of the properties of stem cells is their capacity to migrate after infusion to one or more appropriate microenvironments. Certain stem cells are able to exit their production site, circulating in the blood before reseeding in their target tissues. For mesenchymal stem cells, the nature of homing sites and circulation into peripheral blood is still under debate. However, mesenchymal stem cells have been found after infusion in multiple tissues, leading to the hypothesis that they can home, and that they adjust their differentiation pathways to diverse tissue microenvironments.

In the last decade cellular therapy for cardiac repair has undergone rapid transition from basic science research to clinical reality. The approach to cardiac repair based on stem cells was first realized via early studies that induced in-vitro differentiation of stem cells into cardiomyocytes. Orlic et al. first reported that injection of bone marrow cells with specific markers ($Lin^-/c-kit^+$) to hearts following induction of myocardial infarction resulted in reconstitution of 68% of the infarcted myocardium, the formation of new blood vessels, improvement in left ventricle function and attenuation of remodeling (Orlic D, Kajstura J, Chimenti S, Jakoniuk I, Anderson S M, Li B, Pickel J, McKay R, Nadal-Ginard B, Bodine D M, Leri A, Anversa P. *Bone Marrow Cells Regenerate Infarcted Myocardium*. Nature. 2001; 410:701-5. In another study MSCs were injected intravenously into rat hearts (Bittira B, Shum-Tim D, Al-Khaldi A, Chiu R C. *Mobilization and Homing of Bone Marrow Stromal Cells in Myocardial Infarction*. Eur. J. Cardiothorac Surg. 2003; 24(3):393-8). It was found that labeled cells were seen in and near the infarct up to eight weeks post myocardial infarction, while none was seen in sham-operated hearts. It was concluded that following myocardial infarction, mesenchymal stem cells are signaled and recruited to the injured heart, where they undergo differentiation and may participate in the remodeling process.

SUMMARY OF THE INVENTION

In embodiments of the present invention, bone marrow is irradiated in vivo in order to treat a variety of disease conditions. The irradiation may be performed by transcutaneous application of infrared laser radiation over the area of a marrow-containing bone. Alternatively, other radiation sources may be used, including both coherent and incoherent sources, at both IR and other wavelengths. Although transcutaneous irradiation has the advantage of being non-traumatic, the irradiation may alternatively be applied directly to the bone marrow using invasive techniques.

There is provided according to embodiments of the invention a method of phototherapy, which is carried out responsively to a determination that an injured tissue exists in a body of a living subject by irradiating marrow within a bone in the body that is remote from the injured tissue with biostimulatory radiation of sufficient intensity to engender repair of the injured tissue. The bone may be the tibia, although other marrow-containing bones, e.g., sternum, vertebrae, and pelvic bones may also be subjected to the biostimulatory radiation.

According to an aspect of the method, irradiating is performed by delivering visible or infrared light energy to the marrow by positioning a probe including a source of coherent light on a body surface of the subject, and transcutaneously directing the energy from the probe toward the marrow. The source of coherent light may be a laser or a light-emitting diode. The energy may be directed in a continuous wave mode of operation or in a pulsed mode of operation.

According to a further aspect of the method, the injured tissue may be cardiac tissue or renal tissue.

According to another aspect of the method, irradiating is performed by delivering visible or infrared light energy to the marrow by positioning a laser probe beneath a body surface of the subject, and directing the energy from the probe toward the marrow.

According to yet another aspect of the method, positioning the laser probe is performed by inserting a distal portion of the probe into a medullary cavity of the bone.

According to an additional aspect of the method, irradiating includes positioning multiple laser probes on the subject and directing the radiation from the multiple laser probes to the marrow simultaneously.

According to still another aspect of the method, the bone includes a plurality of bones, including at least a first bone and a second bone, wherein irradiating includes directing first and second ones of the multiple laser probes to the first bone and the second bone, respectively.

According to yet another aspect of the method, the radiation has a wavelength between 630-910 nm.

According to an additional aspect of the method, the radiation has a wavelength of 660 nm.

According to a further aspect of the method, the radiation has a wavelength between 790-830 nm.

According to still another aspect of the method, the radiation has a wavelength of 804 nm at a power of 10 mW/cm2 and an exposure duration of 100-120 seconds.

According to a further aspect of the method, a beam diameter of the radiation within the marrow is 0.3 mm.

According to an additional aspect of the method, irradiating is performed multiple times according to a cyclic dosage schedule. The cyclic dosage schedule may include six doses administered twice a week.

There is further provided according to embodiments of the invention a method of phototherapy, which is carried out responsively to a determination that an injured tissue exists in a living subject by delivering visible or infrared light energy to bone marrow in a bone of the subject at a dose sufficient to cause mesenchymal stem cells to appear in the injured tissue.

There is further provided according to embodiments of the invention an apparatus for administration of phototherapy, including a transparent output interface, which is configured to be brought into contact with a skin surface overlying a bone in a body of a human subject, and a source of coherent light that emits visible or infrared biostimulatory radiation through the output interface so as to irradiate marrow within the bone at a sufficient intensity to engender tissue repair at a location in the body that is remote from the bone.

An aspect of the apparatus includes a flexibly molded appliance adjustable to fit the body and having a plurality of openings therein, wherein the source of coherent light includes a plurality of probes receivable in the openings and directed by the openings to emit infrared or visible radiation through the skin surface toward the marrow.

According to a further aspect of the apparatus, the source of coherent light comprises at least one Gallium Aluminum Arsenide laser.

According to aspect of the apparatus, the radiation has a wavelength between 630-910 nm.

According to one aspect of the apparatus, the radiation has a wavelength between 790-830 nm.

There is further provided according to embodiments of the invention an apparatus for administration of phototherapy, including a flexible probe adapted for insertion into a medullary cavity of a bone in a body of a human subject. The probe has a partially cladded distal portion for exit of laser light radially throughout the distal portion for irradiation of the medullary cavity, and a source of coherent light, generating sufficient visible or infrared light energy to stimulate mesenchymal stem cells in the irradiated medullary cavity to facilitate repair of remotely injured tissue of the subject.

According to still another aspect of the apparatus, the light energy has a wavelength between 630-910 nm.

According to yet another aspect of the apparatus, the light energy has a wavelength between 790-830 nm.

According to a further aspect of the apparatus, the source of coherent light includes at least one Gallium Aluminum Arsenide laser.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, and control logic have not been shown in detail in order not to obscure the general concepts unnecessarily.

System Architecture

The inventors have found in animal experiments that transcutaneous IR irradiation of the bone marrow is effective in promoting tissue recovery following myocardial infarction. Without being bound by any particular theory, the following discussion is offered to facilitate understanding of the invention: It is believed that in vivo irradiation of the bone marrow at sufficient intensity may stimulate growth of stem cells, which migrate to the disease site and participate in repair of the damaged heart tissues. The scope of the present invention, however, is not limited to treatment of myocardial infarction. Rather, embodiments of the present invention may be applied in treating a variety of diseases, irrespective of the precise physiological mechanisms that are stimulated by bone marrow irradiation.

Recruiting stem cells from autologous BM to targeted ischemic or injured organs, e.g., brain or muscles, using the LLLT techniques disclosed herein may inhibit degeneration in diseases such as amyotrophic lateral sclerosis, muscular dystrophy, Parkinson's disease, brain trauma, multiple sclerosis, and stroke. The mechanisms may include replacing lost cells, attenuating degeneration by growth factors that might be produced by the recruited stem cells or any other type of cells in the bone marrow. As described in U.S. Pat. No. 6,395,016, which is herein incorporated by reference, the laser may also cause stimulation of the activity of any type of laser-treated cell, increase its survival after homing into the injured site, attenuate the differentiation of any type of cell to other kind of cell or cause certain cell type to increase the rate of secretion of growth factors either in the bone marrow, the blood or the homing site.

There are also many other degenerative and ischemic diseases and traumatic conditions that involve loss of function, for example in the liver, kidneys, digestive tract, bones etc. It is shown in the experiments described below that MSCs stimulated by LLLT home in specifically on injured/ischemic organs. It is expected that LLLT to the BM may also be helpful in these diseases too.

Figure 1:
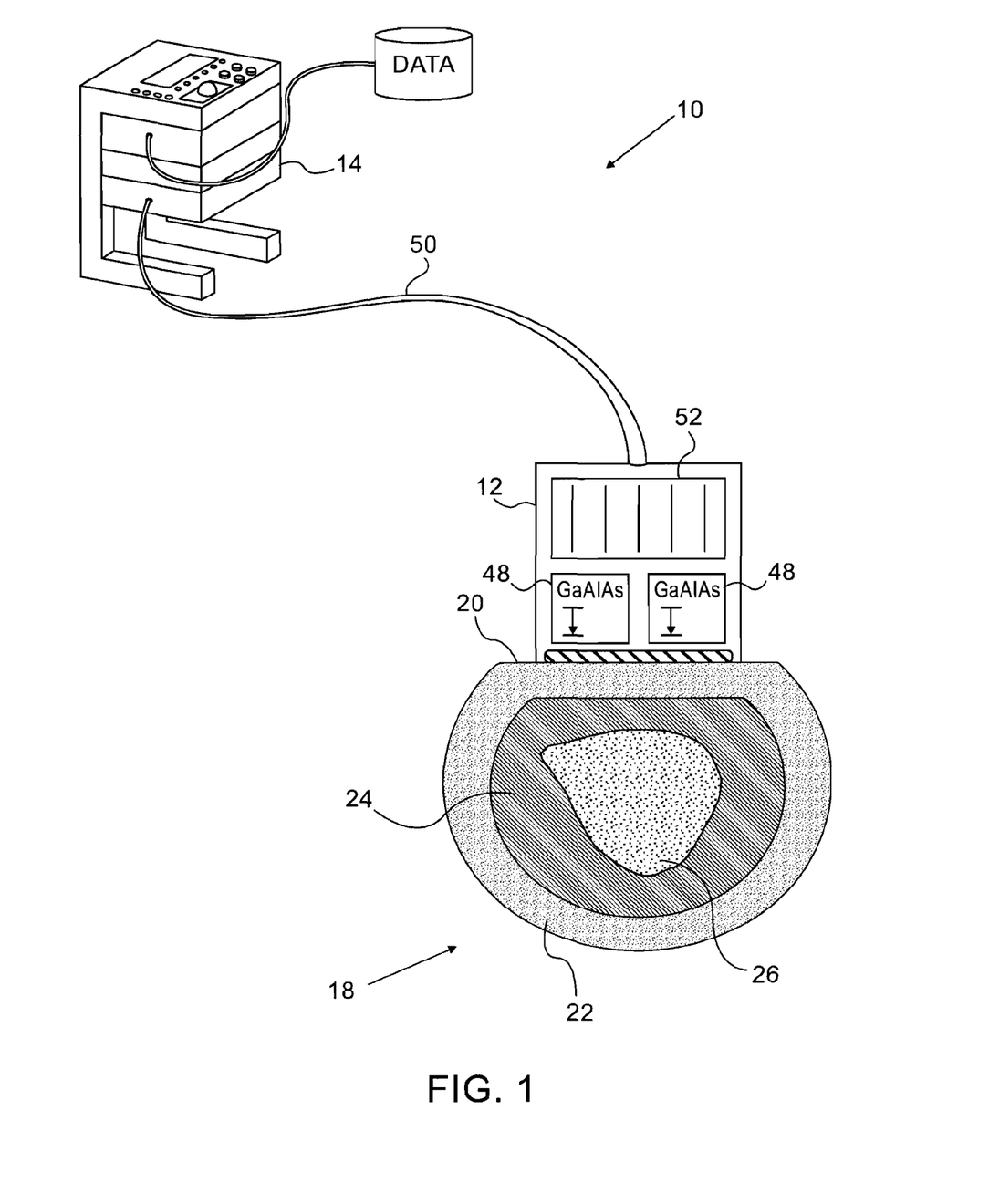
FIG. 1 is a pictorial diagram of a light irradiation system, which is constructed and operative in accordance with an embodiment of the invention.

Turning now to the drawings, reference is initially made to FIG. 1, which is a pictorial diagram of a light irradiation system 10, which is constructed and operative in accordance with an embodiment of the invention. A source of coherent light is linked to a control unit 14. The source may be a laser probe 12 as shown in FIG. 1. Alternatively, the other forms of coherent light may be used, e.g., solid state devices such as light-emitting diodes (LEDs). The laser probe 12 delivers low-level light output to a target tissue, details of which are presented below. The control unit 14 regulates the dosage of the light output as to intensity, duration, and time schedule. While the system 10 is shown in FIG. 1 as two separate components, this is exemplary. The control unit 14 and the laser probe 12 may be integral. For example the system 10 may be realized as a single, hand-held device. The laser may operate in a pulsed mode or a continuous wave mode of operation. An energy dose delivered in pulsed mode penetrates thick bones better and with less local heating than continuous wave mode for a given power output. Laser output devices described in U.S. Pat. No. 6,395,016 are suitable for the laser probe 12.

Optionally, the system 10 includes or is linked to a storage device that holds data generated by the control unit 14. Such data may be used for research purposes, to aid treatment analysis, or to support business requirements of the therapeutic applications delivered by the system 10.

The target tissue is typically a marrow-containing bony structure. The example of FIG. 1 illustrates a transverse section through the shaft of tibia 18. The laser probe 12, shown facing the medial surface of tibia 18, is positioned against or proximate skin 20, soft tissues 22 and bony cortex 24, the target tissue being bone marrow tissue in medullary cavity 26. It is recommended, but not essential, to apply energy to bone marrow tissue having hematopoietic marrow, e.g., bones of the pelvic girdle or the sternum in adult subjects. When dealing with young children, long bones such as the tibia may be chosen for convenience. The skin of the medial tibia is particularly advantageous as there is relatively little intervening soft tissue.

Figure 2:
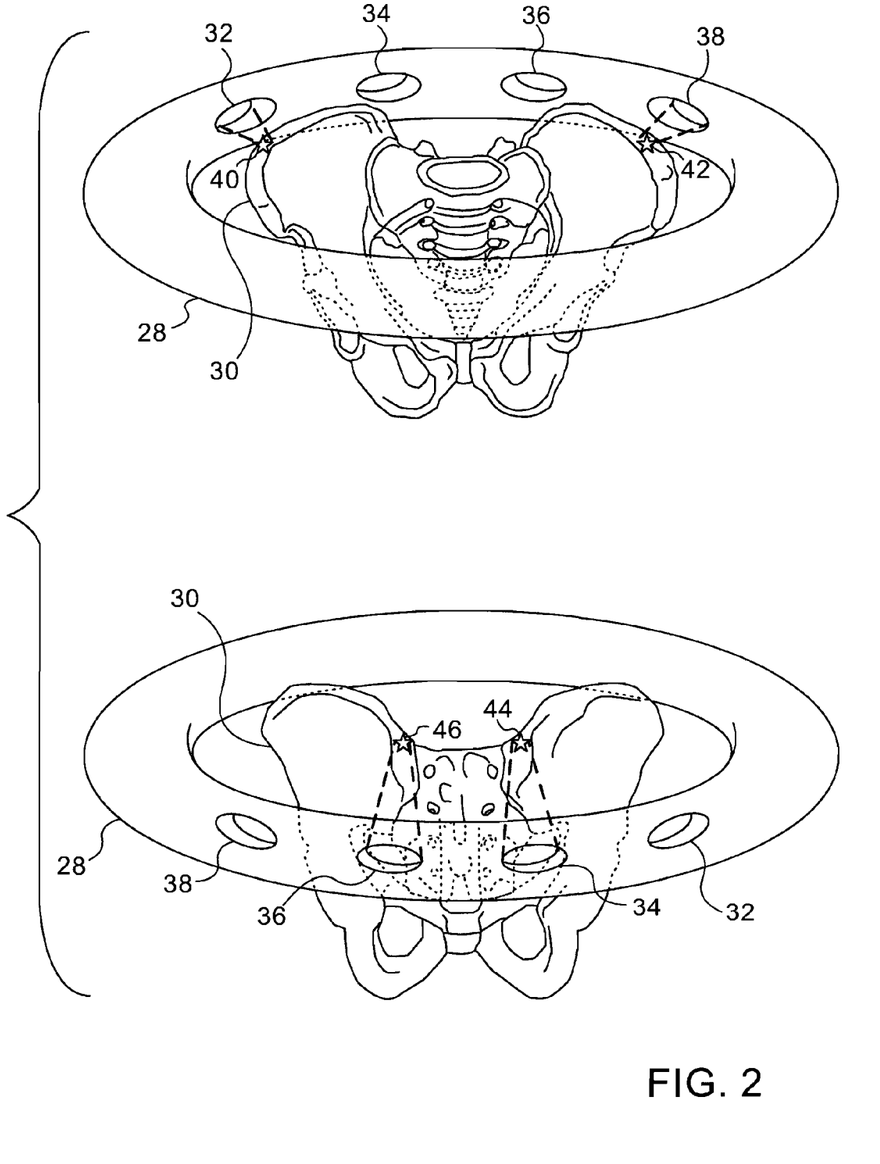
FIG. 2 illustrates an appliance for alignment of therapeutic laser output with desired locations in the human iliac bone.

Reference is now made to FIG. 2, which schematically illustrates an appliance 28 for alignment of therapeutic laser output with desired locations in the human iliac bone. The appliance 28 is shown superimposed on anterior and posterior views of an iliac bone 30 in the upper and lower portions of the figure, respectively. The appliance 28 can be realized as a mold made of silicon (or similar material) to be fitted around the pelvic girdle of a patient. Fixed openings or slots 32, 34, 36, 38 in the appliance 28 are adapted to receive respective laser probes (not shown) therein and direct the output energy to an intended target. While four slots are shown representatively in FIG. 2, the appliance 28 may have any number of slots. Laser light exiting slots 32, 38 may be directed to desired locations on the iliac bone 30, for example points 40, 42 on the anterior iliac crest, as best appreciated in the upper portion of FIG. 2. Laser probes in slots 34, 36 may be aimed at points 44, 46 on the posterior iliac crest as shown on the lower portion of FIG. 2.

Those skilled in the art can modify the appliance 28 for application of laser therapy to other bones, such as the ribs, vertebrae and sternum, all of which normally contain active bone marrow. Indeed, the appliance 28 may be elaborated into a body vest suitable for laser application to many bones simultaneously.

Reverting to FIG. 1, the light application may be non-invasive, or invasive. In the latter case the geometry of the probe is adapted to insertion through a skin puncture or incision. Further alternatively, the light may be delivered via a probe or trephine that can penetrate the cortex 24 for application directly into the medullary cavity 26, using known light-handling techniques such as fiberoptics.

A light source may comprise one or more diode lasers 48 disposed in the laser probe 12. Alternatively, although not illustrated in FIG. 1, the lasers may be disposed in the control unit 14. In the latter case, fiberoptic channels may be incorporated in cable 50 for delivery of the radiation through the probe. The lasers 48 are preferably configured to deliver light in the near infra-red spectrum. However known sources of coherent light that emit in the visible spectrum may also be used.

Optionally, the laser probe 12 may be fluid-cooled in order to minimize discomfort and to avoid the possibility of burning the skin during application. For example, a heat radiator 52 may be provided. Other known air or liquid cooling techniques are also suitable.

The following considerations apply in the design of the light delivery system:

1. In embodiments employing fiberoptic delivery, the tip of each fiberoptic channel should have a relatively large diameter (1-2 cm) to avoid heating of the skin upon placement.

2. The laser probe 12 should insure "full contact" between the output interface of the probe and the skin. To this end the laser probe 12 may be constructed by adaptation of the teachings of U.S. Pat. No. 5,149,955 and U.S. Patent Application Publication No. 2010/0053391, which are herein incorporated by reference.

3. The apparatus should have the ability to deliver 50 mW to 7 W of optical power at the tip of the probe. For non-invasive applications, an output power level in excess of 1 W is desirable, in order to deliver an energy dose of sufficient intensity to engender tissue repair at a location in the body that is remote from the bone. Delivery of at least 10 $mW/cm^2$ to the bone marrow is needed for this purpose. Yet, 12-14 $mW/cm^2$ seems to have a beneficial effect at least as good as 10 $mW/cm^2$ When light is radiated directly into the medullary cavity 26, probes with energy levels at the lower end of the range are sufficient.

4. An emergency "shut off" button should be provided on the laser probe 12 or the control unit 14.

5. The lasers 48 may be GaAlAs lasers, for emission at wavelengths of about 790-830 nm. Other biostimulatory wavelengths between about 630-910 nm can also be used. The radiation output may be either continuous-wave or pulsed.

Alternate Embodiment 1

Figure 3:
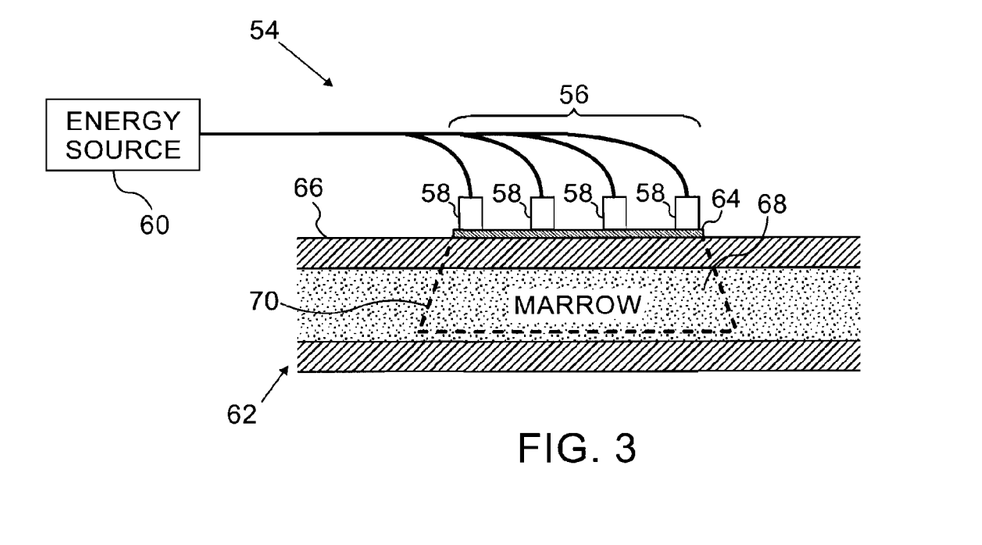
FIG. 3 is a pictorial illustration of a light irradiation system, which is constructed and operative in accordance with an alternate embodiment of the invention.

Reference is now made to FIG. 3, which is a schematic, pictorial illustration of a light irradiation system 54, which is constructed and operative in accordance with an alternate embodiment of the invention. In this embodiment a radiation delivery unit 56 comprises multiple laser probes 58. The delivery unit 56 is connected to a suitable energy source 60. The probes 58 are spaced apart on the body surface or on the surface of a marrow-containing bone 62. An optional mounting plate 64 for the probes 58 is shown in contact with periosteum overlying cortex 66. The plate 64 may be suitably fenestrated to accommodate the probes 58. Alternatively, the plate 64 may be and may be solid and transparent to light at the output wavelength of the probes 58. The plate 64 may be constructed using flexible materials in order to assure good contact between the probes 58 and irregular bone or body surfaces. As discussed above, a portion of the radiation emitted by the probes 58 penetrates into marrow cavity 68. In any case, advantages of the system 54 when compared with a single probe are increased flux of radiation delivered to a therapeutic radiation field 70 in the marrow cavity 68 and a more uniform distribution of radiation throughout the field 70.

Therapy may be administered using multiple instances of the delivery unit 56 simultaneously in the same or different body sites, for example one delivery unit 56 on each tibia. Many combinations involving different bones will occur to therapists skilled in the art.

Alternate Embodiment 2

Figure 4:
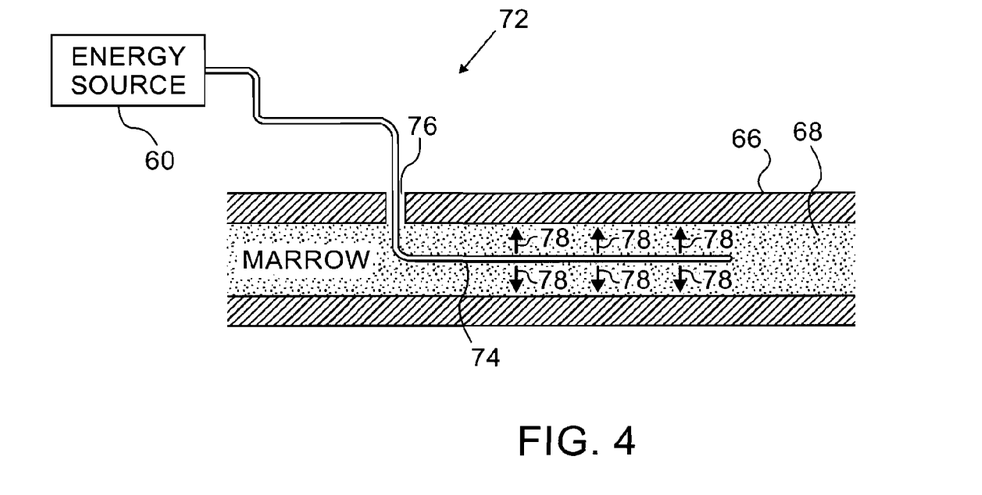
FIG. 4 is a schematic, pictorial illustration of an intramedullary light irradiation system, which is constructed and operative in accordance with an alternate embodiment of the invention.

Reference is now made to FIG. 4, which is a pictorial illustration of an intramedullary light irradiation system 72, which is constructed and operative in accordance with an alternate embodiment of the invention. A flexible fiberoptic probe 74 is inserted through a hole 76 that is drilled through the cortex 66 into the marrow cavity 68. The distal portion of the probe 74 is partially cladded using any suitable incomplete, cladding arrangement, for example having discrete openings, circumferential or longitudinal slots that enable radiation to escape radially, preferably in all directions from the probe 74 along the length of the distal portion, as represented by arrows 78. The fiber can be incorporated in a modified version of the multi-lumen bone marrow aspiration that is taught in U.S. Pat. No. 6,849,051, which is herein incorporated by reference.

This embodiment has the advantage of delivering energy to the marrow more efficiently than the non-invasive embodiments described above, but carries the risk of infection, pain and other possible complications. As in the other embodiments, the power is adjusted to deliver a desired dose to the marrow cavity 68. The system 72 can operate at lower power than the non-invasive embodiments described above.

Operation

Figure 5:
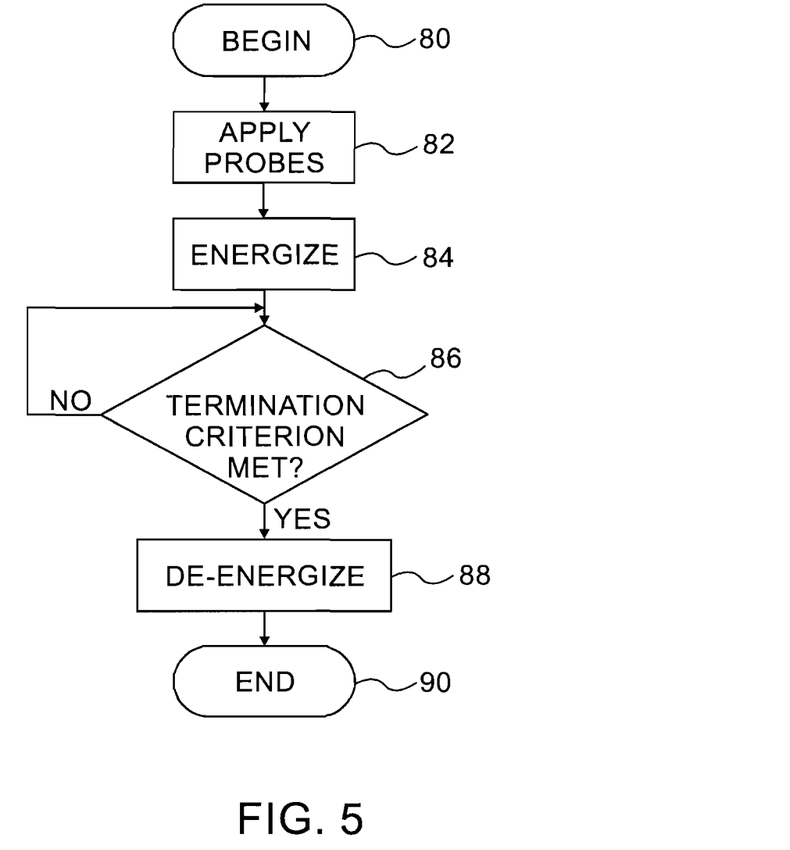
FIG. 5 is a flow chart of a method for delivering low-level coherent light therapy to the bone marrow of a living subject in accordance with embodiments of the invention.

Reference is now made to FIG. 5, which is a flow chart of a method of phototherapy for delivering low-level coherent light therapy to the bone marrow of a living subject, which can be practiced with any of the above-described embodiments.

The process begins at initial step 80. It is assumed that the subject has been shown to have a medical indication for phototherapeutic stimulation of bone marrow tissue. Conventional preparation of the selected sites is undertaken, according to whether invasive or non-invasive techniques are to be employed. This may involve, for example, a surgical incision and perforation of the cortex of a bone in the case of invasive techniques. Baseline tissue samples for monitoring the effect of the procedure may be collected.

Next, at step 82 one or more laser probes are applied to each of the prepared sites and connected to a suitable energy source. A cyclical dosage schedule may be programmed into the control unit of the system to take into account local heating effects and the need to temporarily interrupt the energy flow to avoid cellular injury from overheating. Suggested dosage intervals, laser output wavelengths, power levels and cumulative doses are noted above, and described with particularity in Experiments 1, 4 and 8, and elsewhere in the disclosure below.

Next, at step 84 the probes are energized and irradiation is begun. A timer or other indicator of a termination criterion may be activated, for example a detector of temperature elevation of the probe, tissue heating, or expiration of a time interval.

Then, at delay step 86, it is determined if a termination criterion has been achieved. If so, then at step 88 the probe is de-energized.

At final step 90 the probes are withdrawn from the subject. Another set of tissue samples may be collected at this time, and the process terminates. Generally the process is iterated following injury. After each iteration, the tissue samples may be tested to determine the number of MSCs using the assay techniques described above. Additionally or alternatively the injured tissue or organ may be subjected to tests to determine its status responsively to the irradiation. For example, in the case of myocardial infarction, functional tests such as ejection fraction determination, normalization over time of electroanatomic parameters, and normalization of blood enzymes may be used as indicia of the effectiveness of the irradiation. The dosage intervals and amounts may be adjusted in accordance with deviations of the one or more of such tests from expected results.

Various markers may be used for semiquantitative follow up of the extent of the damage to the patient's heart after MI. Several known markers can be found in the blood. Damage to the heart is correlated with blood marker accumulation over time subsequent to MI. Troponin-T or Troponin-I determinations in the blood or more precisely their accumulation in the blood during the first week post-MI can serve as an estimate both of heart damage and an aid to the estimation of the supportive benefit derived from LLLT.

Another marker is the measurement of the amount of the total antioxidants in the blood of the patients post MI, usually measured daily. It is known that in dogs post-MI that the level of antioxidants in the blood is inversely related to the extent of scarring. Measurements of antioxidants in the blood of the patients may also serve also as a useful marker of the effect of the laser treatment, and support decisions to vary the schedule of multiple LLLT applications post MI. Additionally or alternatively, the commonly used echocardiographic (ECHO) studies of heart function can be performed in patients. Comparison of pre- and post-MI ECHO studies prior to and during the course of LLLT treatments can aid clinical decisions regarding continuation or variation of LLLT treatments, e.g., by changing laser output parameters.

Medical Applications

The clinical application of LLLT to humans following myocardial infarction is expected to be performed as follows: Patient will receive a first laser treatment as described above, followed by multiple additional laser applications to the BM at intervals as described below in Experiment 6. Multiple applications are preferred as they are believed to maximize migration of stem cells to the injured heart (or other affected sites) following the ischemic injury.

Another indication for treatment using embodiments of this invention arises in human newborns, who have experienced transient intra-partum ischemia for various reasons known in the obstetrical art, with resultant insult to the brain and the likelihood of subsequent neurological impairment. Such newborns may benefit neurologically from multiple laser applications to the tibia using the method disclosed with respect to FIG. 5 or as described below in Experiment 7.

Following BM transplantation there might be a delay in the production of BM cells. It was demonstrated in Experiment 1, described below, that LLLT enhances the proliferation of MSCs. It can therefore be postulated that LLLT to the BM may also enhance the production of various other types of marrow cells and the survival of such cells. LLLT may accordingly improve function of the immune system and the numbers of circulating blood cells in laser-treated patients, especially in the early post-BM transplantation period.

As a further application for the phototherapeutic techniques disclosed herein, various chemicals, growth factor, and cells other than MSCs that are stimulated by the treatments and can be isolated from the bone marrow, blood or lymphatic circulation of experimental animals or patients may be used as a drug or for cell therapy purposes to mediate repair or functional improvement of many non-traumatically diseased or traumatized organs in the body.

Experiments

The following animal experiments were conducted to evaluate treatment of the heart.

Experiment 1

The aim of this experiment was to investigate the effect of laser application to bone marrow (BM) in vivo on MSC proliferation capacity when cultured in vitro; and the possibility that low level laser therapy application to autologous BM can induce and recruit MSCs to the infarcted rat heart, reduce scarring post myocardial infarction (MI), and stimulate blood vessel formation in hearts following MI.

A total of 24 Charles River male rats weighing 200-250 gm, underwent ligation of the anterior descending branch of the left coronary artery (LAD) to induce MI, as described previously (U. Oron, T. Yaakobi, A. Oron, G. Hayam, L. Gepstein, T. Wolf, O. Rubin, and S. A. Ben-Haim, *Attenuation of Infarct Size in Rats and Dogs after Myocardial Infarction by Low-Energy Laser Irradiation*. Lasers Surg. Med. 28:204-211.2001). Briefly, rats were anesthetized with Avertin (1 ml/100 g body weight I.P.) and lung ventilated. Thoractomy was performed by incision of the intercostal muscles between the 5th and 6th ribs and the heart was exposed. The LAD was occluded with 5-0 polypropylene thread (Ethicon Inc., Cincinnati, Ohio). Following LAD occlusion the thorax and chest were closed and the rats were ventilated until regaining consciousness. Food and water were supplied ad libitum.

A diode (GaAlAs) laser, wavelength 804 nm with a tunable power output of maximum of 400 mW (Lasotronic Inc., Zug, Switzerland) was used. The laser device was equipped with a metal-backed glass fiber optic (1.5 mm diameter). An infrared viewer (Lasotronic Inc. Zug, Switzerland) and infrared-sensitive detecting card (Newport, Inc., Irvine, Calif.) were used to determine the infrared irradiation area.

LLLT to the BM was performed by placing the distal tip of an optical fiber directly on the middle portion of the medial part of the tibia after making a small incision in the skin. The beam diameter of the laser within the bone marrow was 0.3 cm after transmission through the medial part of the tibia. The power of irradiation on the BM was set to 10 mW/cm$^2$ and the exposure duration was 100 sec (comprising 1 J/cm$^2$). Control rats underwent the same procedure as the laser-irradiated group but the laser was not turned on. Control and laser-irradiated rats were chosen at random. The above parameters of laser irradiation were kept constant in all experiments. Nineteen days post-irradiation, the rats were sacrificed and the hearts were excised.

BM was removed from laser-treated and sham-treated MI-induced rat hearts. MSCs isolation was performed essentially as described by Davani et al., Circulation 2003; 108[suppl II]:II-253-II-258. Mesemchymal progenitor cells differentiate into an endothelial phenotype enhance vascular density and improve heart function in a rat cellular cardiomyoplasty model. The BM was removed using a stainless steel rod that was pushed through the BM cavity. The collected BM was incubated in a shaker with 5 ml medium containing type I collagenase (250 U/ml, Sigma, Israel) for 45 min at 37° C. Cells were then cultured at $1.3 \times 10^6$ cm$^2$ in Dulbeco Modified Eagle Medium (DMEM) supplemented with 10% fetal bovine serum (FBS), 2 mmol/1 L-glutamine, 100 U/ml penicillin, 100 U/ml streptomycin (Biological Industries, Israel). Forty-eight hours later the medium was replaced to remove non-adherent cells (MSCs are known to be adherent from the above-noted Davani et al. publication), and thereafter replaced every four days. An identical number of cells was cultured in each culture plate for the laser-treated or control non-treated MSCs at this point. The MSCs were then cultured for one week, harvested from the culture plates and counted.

As shown in Table 2, the number of cells that were counted in the laser-treated group seven days after culturing was significantly higher (1.5-fold; p=0.006) compared to cells in the non-laser-treated group.

TABLE 2

|  | No. of cells ($10^{-5}$) |
| --- | --- |
| Control | 8.5 |
| Laser-irradiated | 12.5 |

In order to determine the extent of scarring (infarct size) in the heart post-MI, a cross-section sample (1 mm thick) from the central part of the infarcted area was taken from all hearts for histology. Eight-micron paraffin sections were prepared from each tissue sample of each heart. Infarct size and angiogenesis were determined as described previously (T. Yaakobi, Y. Shoshani, S. Levkovitz, O. Rubin, S. A. Ben-Haim and U. Oron. Long-term effect of low energy laser irradiation on infarction and reperfusion injury in the rat heart. J. Appl. Physiol. 90:2411-2419.2001; H. Tuby, L. Maltz, U. Oron. Modulations of VEGF and iNOS in the rat heart by low level laser therapy are associated with cardioprotection and enhanced angiogenesis. Lasers Surg. Med. 38:682-688.2006), using Masson's trichrome staining. Three observers, blinded to control or treated animals, analyzed the area of the infarcted hearts. Infarct size was expressed in percentage as the total infarct area (in mm$^2$) related to the total area of the left ventricle in three random cross-sections of each heart, using image analysis software (Sigma Scan Pro, Sigma, St. Louis, Mo.).

It was found that LLLT to the BM caused a significant (p=0.041) reduction of 36% in average infarct size in the infarcted hearts of the rats that had undergone BM irradiation as compared to those whose BM was not laser-treated (Table 3).

TABLE 3

| | Infarct Size (%) |
|---|---|
| Control | 7.6 |
| Laser-irradiated | 4.8 |

In this experiment, the density of blood vessels in the entire left ventricle including the infarcted area and in the infarcted area alone was also evaluated. LLLT to the BM area in the tibia did not cause a significant (p=0.1, 1.6-fold) elevation in the average density of blood vessels in the non-infarcted portions of the left ventricle in treated rats as compared to the control group (Table 4). In contrast, LLLT to BM caused a significant (p=0.014) elevation of 2.8-fold in the average density of blood vessels (in tissue microscopic sections) in the infarcted area, compared to the control group (Table 5).

TABLE 4

| Non-infarcted portion of LV | |
|---|---|
| | Blood vessels/mm$^2$ |
| Control | 9 |
| Laser-irradiated | 14 |

TABLE 5

| Infarcted portion of LV | |
|---|---|
| | Blood vessels/mm$^2$ |
| Control | 63 |
| Laser-irradiated | 175 |

Kidney and liver tissue samples were also collected from the experimental rats and processed for histology in order to evaluate the appearance of c-kit positive cells in an uninjured organ in rats that had undergone LLLT to their BM. C-kit positive cells express a receptor that is useful as a marker for mesenchymal stem cells. The sections underwent c-kit immunostaining. No elevation of c-kit immunopositivity was observed in the kidneys or liver of laser-treated rats compared to the control group.

It is concluded from this experiment that LLLT can induce cultured stem cells from the BM to proliferate at a significantly higher rate than they would normally proliferate without laser intervention. It is also concluded that laser application about 20 min post-MI to BM can significantly reduce scar formation in the infarcted heart. LLLT to the BM also caused a significant increase in blood vessel density in the infarcted area compared to blood vessel density found in the infarcted area in non-treated rats. MSCs, identified as immunopositive c-kit stained cells, which are biostimulated by the laser migrate to the infarcted heart but do not home in to other injured organs like the liver or kidneys in the same animal.

Experiment 2

The aim of this Experiment was to further explore the beneficial effects of LLLT to BM on the infarcted heart and to follow the fate of the laser-stimulated MSCs from the BM in the heart. This experiment was also designed in order to determine the possible beneficial effects on the infarcted heart of application of LLLT to both the BM and directly to the infarcted heart.

A total of 44 Charles River male rats weighing 200-250 gm underwent ligation of the LAD as described above in Experiment 1. Following MI, rats were divided randomly into four groups: 15 rats served as a sham, non-laser-treated control group; 11 rats were used as a laser-treated group, with the laser applied to the infarcted myocardium, as described in the above-noted Oron et al. publication. Eight rats were used as a laser-treated group in which the laser was applied to the BM in the tibia; and ten rats received laser irradiation both to the BM in the tibia and to the infarcted myocardium. Control and laser-irradiated rats were chosen at random after the induction of MI. Laser irradiation to the BM was performed as described in Experiment 1. LLLT was performed about 20 minutes post-induction of MI to the rats. In the hearts that were laser-irradiated on the infarcted area, laser irradiation was performed by placing the distal tip of a fiber optic probe 4.7 cm from the heart. The beam diameter at the heart was 1.8 cm, so that the total area of the anterior surface of the heart was laser-treated. Power of irradiation was set to 12 mW/cm$^2$ and exposure duration was 100 sec (1.0 J/cm$^2$). Rats were sacrificed 19 days post induction of MI. Sections of rat hearts were stained with Masson's trichrome for infarct size determination as described in Experiment 1.

LLLT to the infarct caused a significant (p=0.001) reduction of 39% in the infarct size compared to control. Laser irradiation to the BM caused a significant (p<0.001) reduction of 79% in infarct size, while in the dual-irradiated rats (on both the BM and the infarcted area in the heart) irradiation caused a significant (p<0.001) reduction of 72% in the infarct size as compared to the control infarcted (non-laser-treated) group. BM (tibia) irradiation showed a significant (p<0.01) reduction of 63% in infarct size and dual irradiation of infarct and BM showed a significant reduction (p<0.01) of 54% compared to infarct irradiation alone. No significant reduction in infarct size was observed between the BM of laser-treated rats and that of those subjected to dual irradiation. These results are summarized in Table 6, in which the results are Results are mean±SEM of 8-15 rats in each column.

TABLE 6

| Effect of LLLT on infarct size | |
|---|---|
| | Infarct Size (% of LV) |
| Control | 35 |
| Laser-irradiated heart | 22 |
| Laser-irradiated BM | 8 |
| Laser-irradiated BM and heart | 10 |

Irradiation of the BM in the tibia of infarcted rats caused a significant (p<0.013) elevation of 2.5-fold in the density of c-kit immunopositive cells in the left ventricle area as compared to the control non-laser-treated rats. Dual laser irradiation to both the BM and the infarcted heart caused a significant (p=0.019) elevation of 3.5-fold in the c-kit positive cell density compared to the control. No elevation in the density of c-kit immunopositive cells was observed in the group that received laser treatment only to the infarcted heart as compared to the control (Table 7). No significant differences in immunopositive c-kit cells were observed between BM irradiation alone compared to dual irradiation of infarcted zone and BM of the tibia.

TABLE 7

| | Cells/mm² in LV |
|---|---|
| Control | 2 |
| Laser-irradiated heart | 4 |
| Laser-irradiated BM | 5 |
| Laser-irradiated BM and heart | 7 |

TABLE 8

| | Cells/mm² in infarcted area |
|---|---|
| Control | 2 |
| Laser-irradiated heart | 13 |
| Laser-irradiated BM | 44 |
| Laser-irradiated BM and heart | 27 |

In the area of the infarcted zone only the BM irradiation caused a significant ($p=0.05$) elevation of 22-fold in the density of c-kit immunopositive cells as compared to the control group. Dual laser irradiation to the BM and infarcted zone caused a significant ($p=0.001$) elevation of 13.5-fold in the density of the density of c-kit positive cells as compared to the control. In the hearts that received laser irradiation on the infarcted zone there was a significant 6.5-fold ($p=0.016$) elevation in c-kit immunopositivity compared to control (Table 8). No significant difference was observed in the density of c-kit in the dual irradiation (on the infarct and BM) compared to BM-laser-treated or infarct laser-treated rats alone and BM irradiation compared to infarct irradiation alone.

C-kit immunopositivity was significantly ($p=0.01$) higher (2.6-fold) in the BM that was laser-irradiated compared to laser treatment of the infarcted heart. No significant difference was observed in the density of c-kit in the dual irradiation (on the infarct and BM) compared to BM-laser-treated or infarct laser-treated rats alone, and in BM irradiation compared to infarct irradiation alone.

Left ventricle dilatation (volume of the left ventricle relative to the heart's total volume) is another marker that correlates with reduction in functional performance of the heart. Left ventricle dilatation was calculated in the present experiment from the microscopic slide sections of the heart in the region of the myocardial infarction. The results are presented in Table 9. The findings indicate that in the non-laser-treated MI-induced hearts the dilatation value was 27%, indicating dilatation of the left ventricle relative to the intact heart with no MI. In the rats with MI that were laser-treated to the BM, the measured value of ventricular dilatation was significantly lower (7%), comprising a reduction of 74% relative to those rats with MI that did not receive the LLLT.

TABLE 9

| | Dilatation (% of LV) |
|---|---|
| Control | 27 |
| Laser-irradiated heart | 19 |
| Laser-irradiated BM | 7 |
| Laser-irradiated BM and heart | 16 |

It is concluded from this experiment that LLLT applied to BM of infarcted rat hearts can reduce the formation of scarring post-MI by 80%, while the application of LLLT to the heart directly reduces scarring to about 60% relative to non-laser-treated infarcted rats. The application of LLLT simultaneously to BM and heart does not give additional benefit over application to BM only. Significantly more MSCs were found in the infarcted hearts of rats that underwent LLLT to their BM than those found in the hearts of non-laser-treated rats. It is also concluded from this experiment that LLLT to BM after MI significantly improves functional performance of the heart, as indicated by a decrease in the dilatation of the left ventricle.

Experiment 3

This experiment was designed to investigate the long-term safety of laser application to the BM on the histology of the BM, liver and kidneys of ICR mice that received laser treatment at several different doses and frequencies compared with two control sham-treated groups of mice.

The laser used in this experiment for all groups was the same as that described for Experiment 1. The mice groups were as follows:

Group 1 (n=11)—Control mice, anaesthetized only once with the laser placed on the tibia but not turned on.

Group 2 (n=10)—Control mice, anaesthetized a total of 6 times, twice a week for 3 weeks. Like Group 1 (above) the laser was not turned on.

Group 3 (n=11)—Laser-treated group. Laser applied only once to the BM in the tibia to deliver 10 mW/cm² power density to the BM for 2 min.

Group 4 (n=5)—Laser-treated group. Laser applied as in Group 3 (above), but for 6 times, twice a week for 3 weeks.

Group 5 (n=5)—Laser-treated group. Laser applied to deliver a dose of 50 mW/cm² for 2 min to the BM only once.

Mice were held under optimal conditions (food and water ad libitum) at room temperature (22-24° C.) for 7-8 months (about 80% of their lifespan) and then sacrificed. The BM, liver and kidneys were fixed in formalin and processed for histology. After staining with hematoxylin-eosin sections, these organs were viewed under the microscope. In the livers of both the control non-laser-treated group and laser-treated group small necrotic centers were noticed, probably due to aging. No histological differences were observed in the kidneys of the laser-treated mice as compared to the controls. In the histological sections of the BM, there was no difference between the control and the laser-treated mice, except for a slight elevation in megakaryocyte density in laser-treated Group 4.

Experiment 4

In this experiment precise measurements of laser irradiation were performed on the tibias of human cadavers to determine the appropriate dose of laser energy to be delivered to the BM in order to achieve a therapeutic effect. The laser used was an infrared laser, wavelength 810-830 nm with power output of 400 mW. Measurements of the power of the laser and its dispersion were made using the equipment described in Experiment 1. Referring again to FIG. 1, the transmission of laser energy from the laser probe 12 to the medullary cavity 26 was 2%. The optimal power density to achieve a therapeutic effect (as described in Experiments 1 and 2) is 12 mW/cm² applied to the BM. Moreover, the laser beam diverged during its passage through the bone from 4 mm diameter at the tip of the fiber optic on the skin to about 20 mm in the medullary cavity 26. In order to correct for these effects, the laser configuration in the laser probe 12 equivalent to a single laser having a beam diameter of 2 cm is required at the laser probe 12 in order to avoid local heating due to high power output. The power output from a probe operating in the configuration of FIG. 1 was about 1.6 W.

Experiment 5

This experiment was designed to determine whether LLLT applied to the BM four hours post-MI would yield a beneficial effect, measured by reduction of scarring relative to non laser-treated rats and in comparison to LLLT applied immediately post-MI as described in Experiments 1 and 2 above.

Twenty-three rats post-MI were used in this experiment. Eight rats received LLLT application to the bone marrow four hours post-MI, while the rest (n=15) served as sham-operated MI-induced controls. The laser parameters and application was identical to those described in Experiments 1 and 2 above. The rats were sacrificed 21 days post-MI and tissue cross-sections from the heart, including the infarcted area, were processed for histology. The histological sections were also stained using c-kit, and quantitative analysis was performed for determination of infarct size, i.e., the extent of scarring and dilatation as described in Experiments 1 and 2.

Table 10 demonstrates that laser treatment to the BM caused a significant reduction in infarct size (52%; p=0.01) compared to the control (non-laser-treated) group.

TABLE 10

| | Infarct Size (%) |
|---|---|
| Control | 25 |
| Laser-irradiated | 12 |

Dilatation measurements, shown in Table 11, were calculated as the ratio of the area of the left ventricular cavity to the total area of the left ventricle, using randomly selected tissue sections from the infarcted area. The results show that dilatation in the laser-treated group was significantly smaller (42%; p=0.018) than in the control group.

TABLE 11

| | Dilatation (% of LV) |
|---|---|
| Control | 33 |
| Laser-irradiated | 19 |

Immunostaining for c-kit, shown in Table 12, indicate that in the entire LV area of laser-treated hearts there was a significantly higher c-kit immunopositive cell density (3.8-fold; p<0.001) compared to the non-laser-treated-group. In the infarcted zone, shown in Table 13, there was a significantly higher cell density (4.2-fold; p<0.001) of c-kit immunopositive cells than in the laser-treated group compared to the control.

TABLE 12

| | Cells/mm$^2$ (in LV) |
|---|---|
| Control | 4 |
| Laser-irradiated | 16 |

TABLE 13

| | Cells/mm$^2$ (in infarcted area) |
|---|---|
| Control | 4 |
| Laser-irradiated | 19 |

In conclusion, this experiment demonstrates that even when laser treatment is applied 4 hours post-MI, there is a significant beneficial effect on the infarcted rat heart over non-treated rats. These results are of clinical significance, allowing treatment to patients within a reasonable "therapeutic window" during which the patient reaches the hospital and MI is diagnosed.

Experiment 6

This experiment is similar to Experiment 5, but the rats were left for 6 weeks until sacrificed. In this experiment MI was produced in 12 rats using the techniques described above. Nine of them were laser-irradiated four hours after MI was induced and the other three were sham-operated. Rats were sacrificed six weeks post-MI. Bone marrow was extracted in order to measure the number of MSCs in the bone marrow 6 weeks post irradiation, and histological sections were taken.

The results indicate no difference in the number of MSCs in BM extracted from the irradiated tibia in the laser-treated group compared to the control 6 weeks post-irradiation (data not shown). Infarct size, shown in Table 14, was significantly smaller (50%; p=0.041) in the laser-treated compared to the non-laser-treated group. Dilatation was not significantly less (32%; p=0.09) in the laser-treated group compared to control, as shown in Table 15.

TABLE 14

| | Infarct Size (%) |
|---|---|
| Control | 14.2 |
| Laser-irradiated | 7 |

TABLE 15

| | Dilatation (% of LV) |
|---|---|
| Control | 19 |
| Laser-irradiated | 13 |

C-kit staining showed a significantly higher density of MSCs (3-fold; p=0.03) in the infarcted zone in the laser-treated group compared to the control group, as shown in Table 16. There was no statistical difference in the MSC density of the entire LV between the laser-treated group and the control group.

TABLE 16

| | Cells/mm$^2$ (infarct) |
|---|---|
| Control | 1 |
| Laser-irradiated | 3 |

Experiment 7

This experiment was designed to determine whether LLLT applied to BM at 7 days post-MI, followed by multiple applications of LLLT at 14 and 21 days post-MI, would yield a beneficial effect (reduction of scarring) relative to non-laser-treated rats and in comparison to LLLT applied immediately as described in Experiments 1 and 2.

MI was induced in 23 rats as described above for this experiment. Nine of them received LLLT to the bone marrow seven days post-MI while the others served as sham-operated MI-induced rats. The laser parameters, application, and evaluation techniques were identical to those described in Experiments 1 and 2. Two additional irradiations were applied on days 14 and 21 post-MI. The rats were sacrificed on day 28. The control group was sham-operated and sacrificed on the same day as the treated group. Tissue sections from the infarcted hearts were processed for histology. The histological sections were stained for c-kit, and quantitative analysis was performed for determination of infarct size (extent of scarring) and dilatation as described in Experiment 1.

There was a significantly higher reduction (57%; p=0.004) in the infarct size from 26% in the non-LT-treated rats to 11% in the LT rats (Table 17). Dilatation was significantly less (36%; p=0.027) in the laser-treated group compared to non-laser-treated controls (Table 18). Moreover, a significant (P=0.004) 2.9-fold increase occurred in the number (per area) of c-kit positive cells in the LV area (Table 19) and a significant (p<0.001) 5-fold increase in c-kit in the infarcted area (Table 20) of the LT rats as compared to the controls.

TABLE 17

| | Infarct Size (%) |
|---|---|
| Control | 26 |
| Laser-irradiated | 11 |

TABLE 18

| | Dilatation (% of LV) |
|---|---|
| Control | 33 |
| Laser-irradiated | 21 |

TABLE 19

| | Cells/mm$^2$ (in LV) |
|---|---|
| Control | 5 |
| Laser-irradiated | 14 |

TABLE 20

| | Cells/mm$^2$ (in infarcted area) |
|---|---|
| Control | 4 |
| Laser-irradiated | 18 |

It is concluded that LLLT applications beginning even a week post-MI with multiple applications thereafter can cause a significant attenuation in scar formation and ventricular dilatation in the infarcted heart. This fact is of clinical significance, and promotes LLLT as a possible treatment for patients with existing post-MI scarring.

Experiment 8

An experiment was performed with infarcted rats to investigate the long-term effect of LLLT to BM in vivo on MSCs proliferation capacity when cultured in vitro three and six weeks post laser application.

A total of 20 Charles River male rats (weight 200-250 g) underwent ligation of the left anterior descending artery to induce myocardial infarction (MI) in the manner described above. The rats were then divided randomly into two experimental groups. Group 1 contained 12 rats: six were laser-treated while the other six (control) did not receive laser treatment. Rats in this group were sacrificed three weeks post-MI. In group 2, four rats served as the laser-treated group and four as a control group. Laser application was carried out 0.5 hours to four days post-MI. These rats were sacrificed six weeks post-MI. BM was removed from both laser-treated and sham-treated tibias of MI-induced rat hearts. MSCs were isolated, incubated for one week, harvested from the culture plates and counted. As shown in Table 21 the number of cultured MSCs that originated from rats three weeks post-laser treatment was significantly higher (1.5-fold; p=0.006) compared with the number of cells that were grown post-isolation from BM. In the 6-week group there was no significant difference between the number of MSCs isolated and grown in culture in the laser-treated or non-laser-treated BM.

TABLE 21

| | | Cells/mm$^2$ |
|---|---|---|
| 3 weeks | Control | 9 |
| | Laser-irradiated BM | 13 |
| 6 weeks | Control | 8 |
| | Laser-irradiated BM | 9 |

In conclusion, these results indicate that three weeks post-irradiation there is still a stimulatory effect of laser irradiation on stem cells in the bone marrow. But six weeks later, the stimulatory effect of the laser treatment on MSCs isolated from the bone marrow no longer exists. Thus the effect of LLLT on MSCs derived from the tibia bone marrow is transient.

Experiment 9

This experiment was designed to estimate the number of total c-kit immunopositive cells in the heart of non laser and laser-treated BM in the rats based on observations from the rats in Experiment 8.

The volume of the rat heart was estimated to be about 1 cm$^3$ containing $10^{10}$ cells of all types. The total number of c-kit positive cells in the laser-treated rats was estimated (based on estimates of heart and tissue section volumes and configurations) to be 1,558,700 cells three weeks post MI. This number was calculated based on average cell number in microscopic sections of the heart of rats as described in Experiment 1. This number was multiplied by the total number of sections in the rat hearts. The number of c-kit positive cells decreased to 58,000 cells in the laser-treated rats at six weeks post-MI. Thus, if it is assumed that the loss of c-kit positive cells is linear from three to six weeks every week, there is a loss of 510,230 MSCs. In the group of rats where multiple laser applications were applied post-MI (Experiment 7) the estimated number of c-kit positive cells was found to be 1,316,000 cells. The interpolated estimated number of MSCs remaining in the heart at four weeks according to the above assumption of loss (510,230 cells per week) is about 1,078,000 cells. Thus, the number of c-kit positive cells found at four weeks post-MI with multiple laser application is greater than this estimated number (1,316,000 cells as compared to 1,078,000).

The number of MSCs as determined by c-kit positivity found in the heart 3 weeks post MI suggest that stem cells migrating to the infarcted heart even in the laser-treated rats are too few to compensate for the stem cells that were lost as a result of the MI. The number of MSCs decreased even further between three and six weeks post MI. As noted above in the section entitled "Medical Applications", the data suggest that multiple laser applications post-MI to the BM may be most likely to achieve cardiac functional improvement in recovering post-MI patients.

Experiment 10

The aim of this experiment was designed to investigate the possible effect of LLLT on the process of formation of adhesions and scar tissue in the area of surgical intervention post surgical procedures.

Twelve rats were used for this experiment. All rats underwent surgical procedure to produce a temporary occlusion of the right renal artery for 15 minutes (three control and five laser-treated rats) or 30 minutes (two controls and two laser-treated) post-renal artery occlusion. The exposure of the kidney was performed by lateral excision in the skin and muscles above the kidney area. Seven rats were treated with LLLT to the BM as described in Experiment 1 at 15 minutes after temporary occlusion of the renal artery, and once again a week later. Sham-treated rats used as controls underwent the same procedure as the laser-treated rats but the laser was not turned on.

The rats were sacrificed 2 weeks post-surgery. Scarring and adhesions in the operative site around the right kidney were examined macroscopically. While in the non laser-treated rats scarring around the kidney and adhesion of the kidney to adjacent tissues (abdominal muscles, liver, etc.) were noticed, there was a marked reduction in scarring and adhesions around the right kidney of the laser-treated rats.

It is suggested that LLLT to the bone marrow may induce proliferation (see Experiment 8) and activation of stem cells or other cells in the bone marrow so that they may migrate to the surgical or traumatized area (via circulating blood) and attenuate the process of scarring, which results in a marked reduction of post traumatic adhesions. This phenomenon is of clinical importance in any surgical procedure in humans where adhesion post surgery may have adverse effects to the body.

Experiment 11

Renal dysfunction occurs in a clinical condition known as nephritic syndrome, which may present as total or partial renal impairment. Such impairment may result from various clinical conditions. The above condition may involve various histological phenomena in various parts of the kidney structures (cortex, nephrons, papillary tubules etc.). Ischemic-reperfusion injuries to the kidney in experimental animals may mimic pathological stages of nephritic syndrome in humans.

The aim of this experiment was designed to investigate the possible effect of LLLT on ischemia-reperfusion injury (IRI) in the kidney. Twelve rats were used for this experiment. All rats underwent surgical procedure to occlude the right renal artery for 15 minutes (three control rats and five laser-treated rats) or 30 minutes (two control rats and two laser-treated rats (prior to renal artery occlusion). The exposure of the kidney was performed by lateral excision in the skin and muscles above the kidney area. Seven rats were treated with LLLT to the BM as described in Experiment 1 at 15 minutes post surgery and once again a week later. Sham-treated rats used as controls underwent the same procedure as the laser-treated rats but the laser was not turned on.

The rats were sacrificed 14 days post-IRI and tissue cross-sections from the right and left kidneys were processed for histology. The histological sections were stained for hematoxylin-eosin. Sections were analyzed by light microscopy. In the 15 min IRI experiment in the control group kidney sections, section the papilla and the medullary part of the kidney had marked histopathological damage. The papilla was diminished and in the medulla there was significant tubular necrosis. In the LLLT sections from rats exposed to LLLT, there was very light injury in the papillary area, while the medulla and the cortex did not show any damage. In the rats experiencing IR injury as a result of occlusion for 30 minutes, the control group showed no papilla, and displayed significant increase in necrosis, large with tubular dilatation in the medulla and cortex, and visible damage in the glomeruli. The sections from the group treated with LLLT showed small injured papillae and necrosis and dilatation of the tubules in the medulla and the cortex.

The 15 min IRI sections were also stained for c-kit. The results showed that in the laser-treated group there was a significant ($p=0.02$) 3.87-fold higher c-kit immunopositive cells per $mm^2$ of tissue section compared to the control group.

It is concluded that LLLT to the BM immediately and 1 week post renal IRI prevents necrosis in the papilla, medulla and cortex and preserves them better when compared with a sham-treated control group.

Experiment 12

The aim of the Experiment was to further explore the beneficial effects of diode laser application at a wavelength of 660 nm (as opposed to 810 nm in Experiment 2) to BM on the scar formation following MI in the rat model.

A total of 12 male Wistar rats weighing 200-250 g underwent ligation of the LAD as described in Experiment 1. The rats were divided after MI into two groups: eight rats served as sham-treated rats served as a control group, and four rats were used as a laser-treated group. Control and laser-treated rats were chosen at random after the induction of MI. Laser irradiation to the BM was performed as described in Experiment 1 using a diode laser, wavelength 660 nm with a tunable power output, maximally 40 mW (Lasotronic Inc., Zug, Switzerland). The laser device was equipped with a metal-backed glass fiberoptic interface (1.5 mm diameter). An infrared viewer (Lasotronic Inc. Zug, Switzerland) and infrared-sensitive detecting card (Newport, Inc., Irvine, Calif.) were used to determine the infrared irradiation area in the BM after transmission through the medial part of the tibia (as described in Experiment 1).

LLLT was applied to the BM about 20 min post induction of MI. The power of laser irradiation on the BM was set to 10 $mW/cm^2$ and the exposure duration was 100 sec (comprising 1.0 $J/cm^2$). Rats were sacrificed 21 days post induction of MI. Sections from rat hearts stained with. Masson's trichrome were analyzed for infarct size determination (as described in Experiment 1).

The laser irradiation on the BM caused a significant ($p<0.001$) reduction of 78% in the infarct size as compared to the control (non-laser-treated) group.

It can be concluded that diode laser application at a wavelength of 660 nm to the BM in rats post MI results in a significant reduction of scar formation. It is also concluded that LLLT application to the BM caused beneficial effect to the IRI kidney in conjunction with significantly greater c-kit immunopositive cell recruitment, similar to the infarcted heart It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method of phototherapy, comprising the step of:
responsively to a determination that an injured tissue exists in a living subject delivering visible or infrared light energy to bone marrow in a bone of the subject that is remote from the injured tissue at a dose sufficient to cause mesenchymal stem cells to appear in the injured tissue, wherein the subject is an adult or a child.

2. The method according to claim 1, wherein the delivering visible or infrared light energy is performed by:
positioning a probe comprising a source of coherent light on a body surface of the subject; and
transcutaneously directing energy from the probe toward the bone marrow.

3. The method according to claim 2, wherein the source of coherent light is a laser.

4. The method according to claim 2, wherein the source of coherent light is a light-emitting diode.

5. The method according to claim 2, wherein directing the energy from the probe is performed in a continuous wave mode of operation.

6. The method according to claim 2, wherein directing the energy from the probe is performed in a pulsed mode of operation.

7. The method according to claim 1, wherein the injured tissue is cardiac tissue.

8. The method according to claim 1, wherein the injured tissue is renal tissue.

9. The method according to claim 1, wherein the delivering visible or infrared light energy is performed by delivering visible or infrared light energy to the bone marrow by:
a laser probe beneath a body surface of the subject; and
directing the energy from the laser probe toward the bone marrow.

10. The method according to claim 9, wherein positioning the laser probe comprises inserting a distal portion of the laser probe into a medullary cavity of the bone.

11. The method according to claim 1, wherein the delivering visible or infrared light energy comprises positioning multiple laser probes on the subject and directing from the multiple laser probes to the bone marrow simultaneously.

12. The method according to claim 11, wherein the bone comprises a plurality of bones, including at least a first bone and a second bone, wherein the delivering visible or infrared light energy comprises directing first and second ones of the multiple laser probes to the first bone and the second bone, respectively.

13. The method according to claim 1, wherein the visible or infrared light energy has a wavelength between 630-910 nm.

14. The method according to claim 13, wherein the visible or infrared light energy has a wavelength of 660 nm.

15. The method according to claim 1, wherein the visible or infrared light energy has a wavelength between 790-830 nm.

16. The method according to claim 1, wherein the visible or infrared light energy has a wavelength of 804 nm at a power of 10-14 $mW/cm^2$ and an exposure duration of 100-120 seconds.

17. The method according to claim 1, wherein a beam diameter of the visible or infrared light energy within the bone marrow is 0.3 cm.

18. The method according to claim 1, wherein the delivering visible or infrared light energy is performed multiple times according to a cyclic dosage schedule.

19. The method according to claim 18, wherein the cyclic dosage schedule comprises six doses administered twice a week.

20. The method according to claim 1, wherein the bone is a tibia.

21. The method according to claim 1, further comprising the step of:
after delivering visible or infrared light energy, testing the injured tissue to determine its status responsively to irradiation.

22. An apparatus for administration of phototherapy, comprising:
a flexible probe adapted for insertion into a medullary cavity of a bone in a body of a human subject, wherein the subject is an adult or a child, the probe having a partially cladded distal portion for exit of laser light radially throughout the distal portion for irradiation of the medullary cavity; and
a source of coherent light connected to the probe, generating sufficient visible or infrared light energy to stimulate mesenchymal stem cells in the irradiated medullary cavity to facilitate repair of remotely injured tissue of the subject.

23. The apparatus according to claim 22, wherein the visible or infrared light energy has a wavelength between 630-910 nm.

24. The apparatus according to claim 22, wherein the visible or infrared light energy has a wavelength between 790-830 nm.

25. The apparatus according to claim 22, wherein the source of coherent light comprises at least one Gallium Aluminum Arsenide laser.

* * * * *